US009241455B2

(12) United States Patent
Dräger et al.

(10) Patent No.: US 9,241,455 B2
(45) Date of Patent: Jan. 26, 2016

(54) TOMATO PLANT COMPRISING A MUTANT TGHVI ALLELE

(71) Applicant: RIJK ZWAAN ZAADTEELT EN ZAADHANDEL B.V., De Lier (NL)

(72) Inventors: Dörthe Bettina Dräger, Den Haag (NL); Zeger Otto Van Herwijnen, Rotterdam (NL); Rudolf Verhoef, Naaldwijk (NL); Arie Vogelaar, Dordrecht (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 248 days.

(21) Appl. No.: 13/761,977

(22) Filed: Feb. 7, 2013

(65) Prior Publication Data
US 2014/0223593 A1    Aug. 7, 2014

(51) Int. Cl.
*A01H 5/08*    (2006.01)
*A01H 1/00*    (2006.01)
*C07H 21/04*   (2006.01)
*C12N 15/00*   (2006.01)

(52) U.S. Cl.
CPC ........................................ *A01H 5/08* (2013.01)

(58) Field of Classification Search
None
See application file for complete search history.

(56) References Cited

PUBLICATIONS

Vardy et al., Genetics of parthenocarpy in tomato under a low temperature regime: II Cultivar 'Severianin', 41 Euphytica 9-15 at 13 (1989).*
Kang et al., Distortion of trichome morphology by the hairless mutation of tomato affects leaf surface chemistry, 61 J of Exp Botany 1053-1064 (2010)).*

* cited by examiner

*Primary Examiner* — Phuong Bui
(74) *Attorney, Agent, or Firm* — Vedder Price P.C.; Thomas J. Kowalski; Deborah L. Lu

(57) ABSTRACT

The present invention relates to a tomato plant (*Solanum lycopersicum* L.) in which the glandular heads of type VI trichomes are absent, and that has a modified composition of flavonoids and volatiles. Furthermore, the typical tomato smell is absent or nearly absent. The plant comprises a mutant allele, which is obtainable from a tomato plant, representative seed of which was deposited under deposit accession number NCIMB 41845. The said mutant allele is located on chromosome 9 between positions 1750800 bp and 4517648 bp, preferably between positions 1939546 bp and 2970346 bp, most preferably at about position 2454946 bp on a physical map of the *Solanum lycopersicum* genome.

21 Claims, 15 Drawing Sheets

| accession | description | nmol glucose/cm² leaf area after saponification |
|---|---|---|
| T012/144 | plant of the invention | 2,0 |
| T012/145 | plant of the invention | 1,8 |
| T012/146 | isogenic plant | 1,6 |
| T012/147 | isogenic plant | 1,4 |
| T012/150 | LA0259 (hl) | 2,0 |
| T012/151 | LA0259 (hl) | 1,7 |
| T012/152 | wild type | 2,1 |
| T012/835 | wild type | 1,5 | unbalanced ANOVA

Analysis of an unbalanced design using Genstat regression

Variate: cis_3_hexenal

Accumulated analysis of variance

| Change | d.f. | s.s. | m.s. | v.r. | F pr. |
|---|---|---|---|---|---|
| + year | 1 | 1.3145 | 1.3145 | 7.40 | 0.022 |
| + type | 3 | 3.0508 | 1.0169 | 5.73 | 0.015 |
| Residual | 10 | 1.7759 | 0.1776 | | |
| Total | 14 | 6.1412 | 0.4387 | | |

Predictions from regression model

Response variate: cis_3_hexenal

| type | Prediction |
|---|---|
| LA0259 | 6.041 |
| plants of the in-cention | 5.331 |
| isogenic plants | 6.697 |
| wt | 6.149 |

FIG. 14

TOMATO PLANT COMPRISING A MUTANT *TGHVI* ALLELE

RELATED APPLICATIONS AND INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a tomato plant (*Solanum lycopersicum* L.) that shows no or a reduced level of green staining and/or no or a reduced smell. The invention further relates to a marker and the use of the marker for identifying tomato plants with this phenotype. The invention also relates to the seeds and progeny of such plants and to propagation material for obtaining such plants. Furthermore the invention relates to the use of the plants, seeds and propagation material that show the phenotype as germplasm in a breeding program.

BACKGROUND OF THE INVENTION

Tomato is a vegetable crop grown worldwide in all conditions and climates, both in protected cultivation or in open field. Growing tomato plants requires a lot of labor and attention, during which the plants are handled repeatedly by various persons. Handling the plants includes activities such as grafting, planting, pruning, winding, and of course harvesting.

Persons working in a tomato crop rapidly notice that with every contact of a green part of the tomato plant, a green substance comes off on the skin or any surface the contact is made with. The substance can also be yellowish in color. Especially hands and clothes become covered with this substance, which after very intensive handling can result in almost black greenish stains on for example the hands. The main difficulty of this substance is that it is very hard to remove from the skin or clothes by normal washing. The green or yellowish substance results in green staining.

Another aspect of a tomato plant is the typical tomato smell that it emits. This can become rather unpleasant when one is frequently exposed to a tomato crop.

The surface of the various plant parts of tomato (*Solanum lycopersicum*) is covered with trichomes, both non-glandular and glandular. Non-glandular trichomes are usually regarded as 'hairs' and do not produce, store, or secrete specific biochemical compounds.

A variety of biochemical compounds in tomato however are produced in glandular trichomes. A glandular trichome typically consists of a stalk, made up of one or more cells, and one or more glandular cells at the tip of the stalk that form the glandular head. Four different types of glandular trichomes are identified in tomato and related *Solanum* species, namely types I, IV, VI, and VII. These types differ in size and length of the stalks, and in number of secretory cells that form the glandular head (McDowell et al., Plant Physiology Vol. 155, 524-539 (2011)). The unicellular glands, which may comprise one glandular cell that forms the glandular head, are classified as secreting glands, while multicellular glands are classified as storage glands.

Type VI trichomes are composed of four disc cells, or glandular cells, at the end of a one- or two-celled stalk. The four disc cells form the multicellular glandular head (FIG. 1).

Biochemical compounds that are produced by the various glandular trichomes in tomato comprise terpenoids, flavonoids, fatty acids, alkaloids, and acyl sugars such as acyl glucoses and acyl sucroses. A substance such as chlorophyll however is not among the compounds known to be produced or secreted by glandular hairs in tomato. The produced compounds are known to play important roles in attracting and repelling various insects and in determining susceptibility to certain diseases. However, many aspects of the roles of these metabolites are still unclear, and extensive research is ongoing to determine more precisely the functionality of glandular trichomes and the substances they excrete.

In addition, data on the distribution of which substances are produced by what type of glandular hairs is rather limited and requires specialized approaches to obtain. For many substances it is assumed that they are or may be produced by several glandular hair types, although it is indicated that there are differences in the quality and quantities that are produced by a certain type of glandular hairs. It is for instance known that acyl sugars, which play a significant role in insect resistance, are mainly produced in tomato type I and IV trichomes.

Citation or identification of any document in this application is not an admission that such document is available as prior art to the present invention.

SUMMARY OF THE INVENTION

It is an object of the present invention to provide a tomato plant (*Solanum lycopersicum* L.) that shows no or a reduced level of green staining and/or no or a reduced typical tomato smell.

It is a further object of the present invention to provide a marker that may identify a plant that has the phenotype of the invention.

The invention provides a tomato plant that may be characterized by the following features:
  the plant does not comprise or has at least a strongly reduced number of the glandular cells of type VI trichomes,
  the plant does not cause green staining upon contact,
  the plant has a strongly reduced level of volatiles, in particular terpenes, sesquiterpenes and aldehydes,
  the plant does not express or is at least strongly reduced in the typical tomato smell, and
  the plant does not comprise or has at least a strongly reduced level of flavonoids.

The present invention also provides a tomato plant (*Solanum lycopersicum*) which may comprise a mutant allele which allele is linked to the following phenotypic features:
  the plant does not comprise or has at least a strongly reduced number of the glandular cells of type VI trichomes,
  the plant does not cause green staining upon contact,
    the plant has a strongly reduced level of volatiles, in particular terpenes, sesquiterpenes and aldehydes,
  the plant does not express or is at least strongly reduced in the typical tomato smell, and
  the plant does not comprise or has at least a strongly reduced level of flavonoids.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Seeds of *Solanum lycopersicum* 11R-5000 that comprise the mutant tghVI allele of the invention were deposited with NCIMB Ltd, Ferguson Building, Craibstone Estate, Bucksburn, Aberdeen AB21 9YA, UK on 13 Jun. 2011 under deposit accession number NCIMB 41845.

The Deposits with NCIMB Ltd, under deposit accession number 41845 were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

During the research that led to the present invention new mutant tomato plants were created through application of an EMS treatment protocol (EXAMPLE 1). The plant that resulted in the invention was identified from the resulting population as it did not leave a green residue or green staining upon touching the green vegetative parts such as leaves or stem. Plant growth and plant type of the new tomato plant were comparable to normal tomato plants. The mutant plant was not considered to be weak in growth or in plant habit. No defects regarding the reproduction of the plant, such as sterility, fruit development, or seed development were observed.

Figure 1:
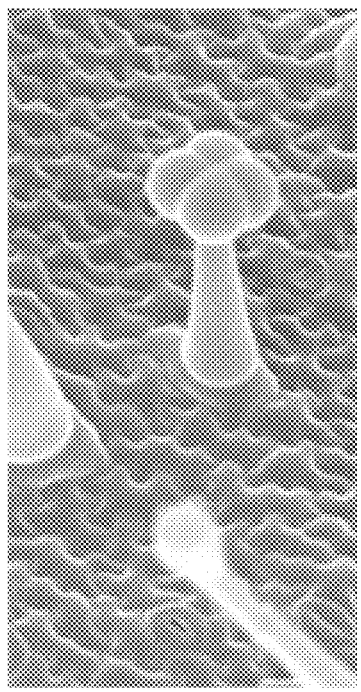
FIG. 1: Type VI trichome *Solanum lycopersicum* (Kang et al. J. Exp. Bot 61(4), 1053-1064, detail Suppl. Material, (2010))
Figure 2A:
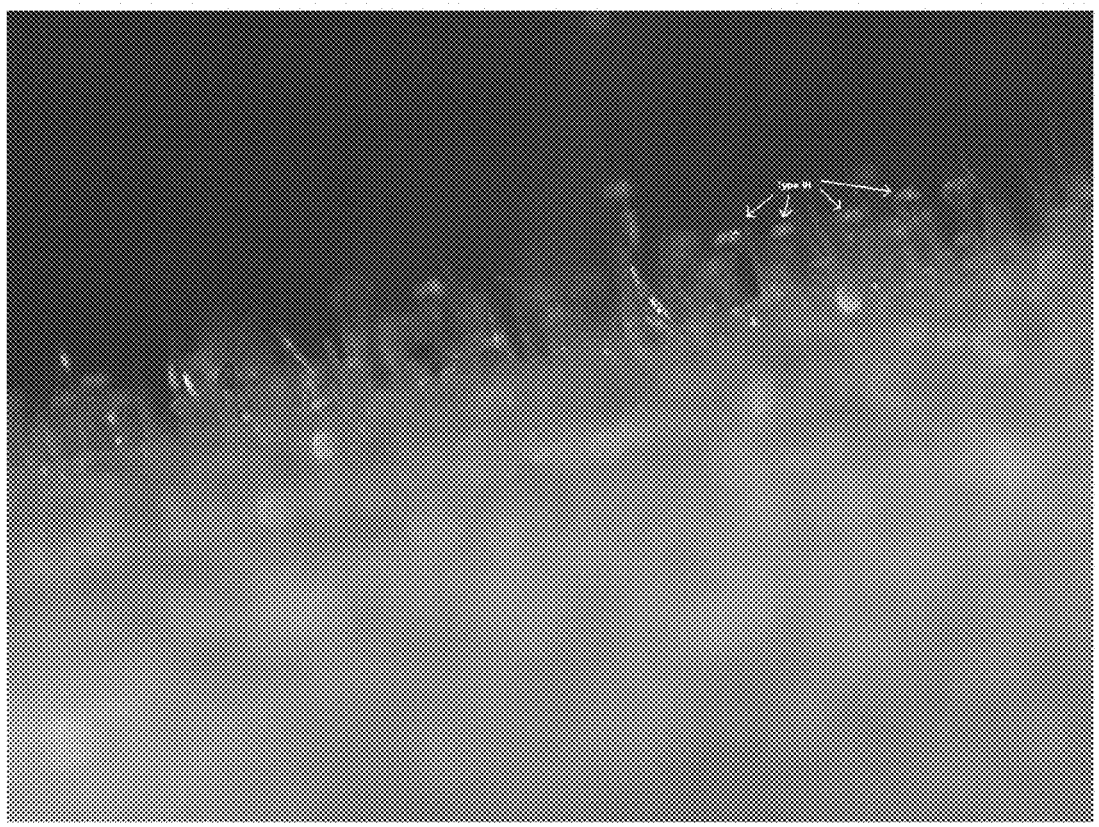
FIG. 2A-2B: A: Wildtype TR306-1 type VI trichomes with glandular head. B: mutant 3432-1 type VI trichomes with glandular heads absent.
Figure 2B:

The new tomato plant was analysed for phenotypical characteristics. The glandular trichomes in cultivated tomato (*Solanum lycopersicum*) that are most abundant are type I and type VI. Surprisingly, the observation of the surface of green plant parts of this particular plant showed that wild type trichomes of type VI could not be detected. The typical glandular heads of type VI trichomes, which are made up of four glandular cells, were not present among the trichomes (FIG. 2B), only the stalks could still be recognized.

It was thus found that in the newly created tomato plant that does not show green staining the glandular cells of type VI trichomes were absent.

It was also found that this specific plant also lacked the typical tomato-plant smell.

Further analysis of the new tomato plants was done to determine the presence of various biochemical compounds. Measurements were done on three groups of volatiles: terpenes, sesquiterpenes, and aldehydes. The analysis showed that the plants of the invention had a significant reduction of nearly all volatiles that were analysed within these groups. Some volatiles could not be detected and are considered to be absent or nearly absent. The biochemical analysis is described in detail in Example 5.

Figure 3:
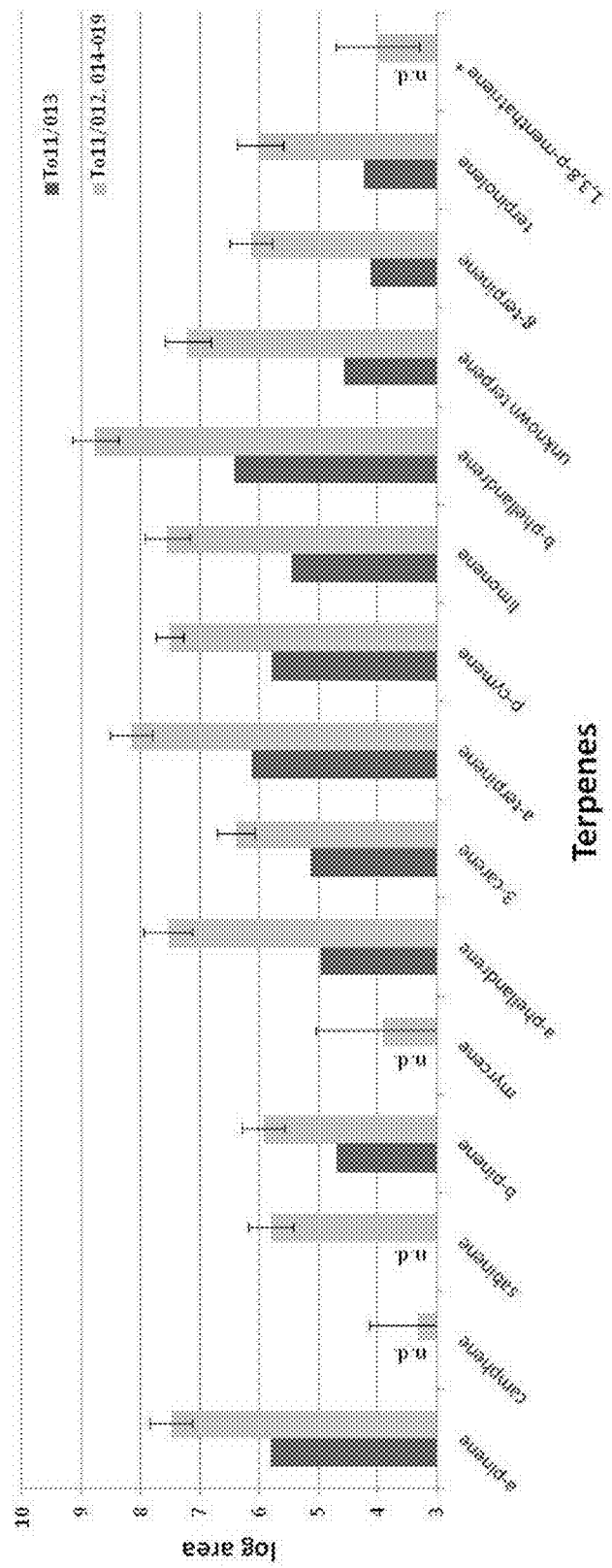
FIG. 3: Measurements in 2011 of various terpenes in plants of the invention (To11/013) as compared to normal wild-type tomato plants (To11/012, To11/014-019); n.d.=not detected
Figure 4:
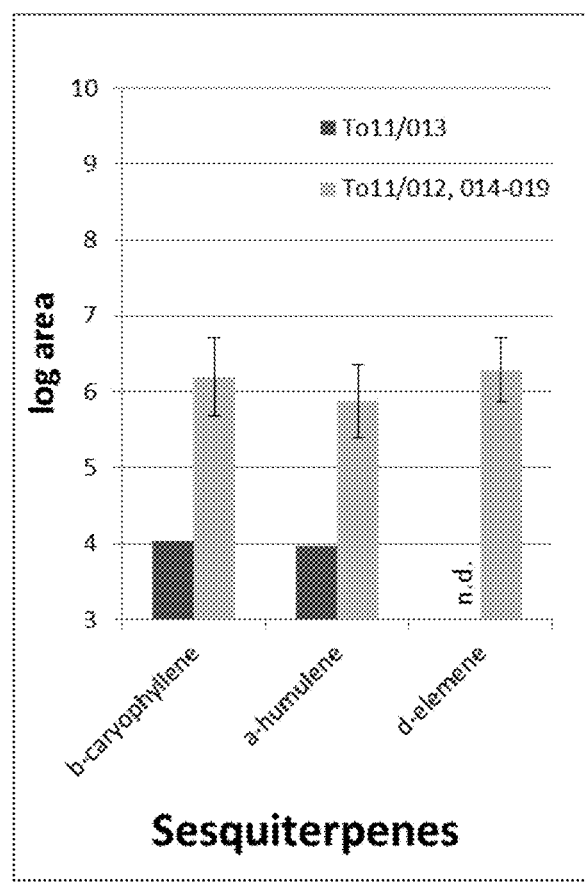
FIG. 4: Measurements in 2011 of various sesquiterpenes in plants of the invention (To11/013) as compared to normal wild-type tomato plants (To11/012, To11/014-019); n.d.=not detected
Figure 5:
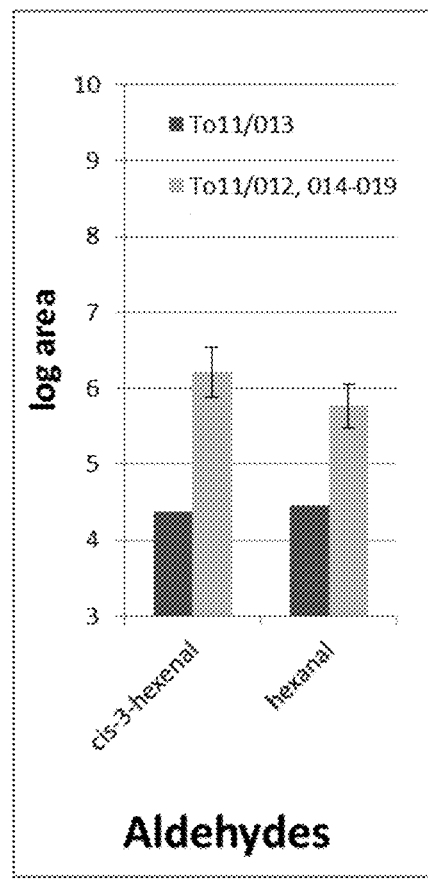
FIG. 5: Measurements in 2011 of various aldehydes in plants of the invention (To11/013) as compared to normal wild-type tomato plants (To11/012, To11/014-019); n.d.=not detected
Figure 8:
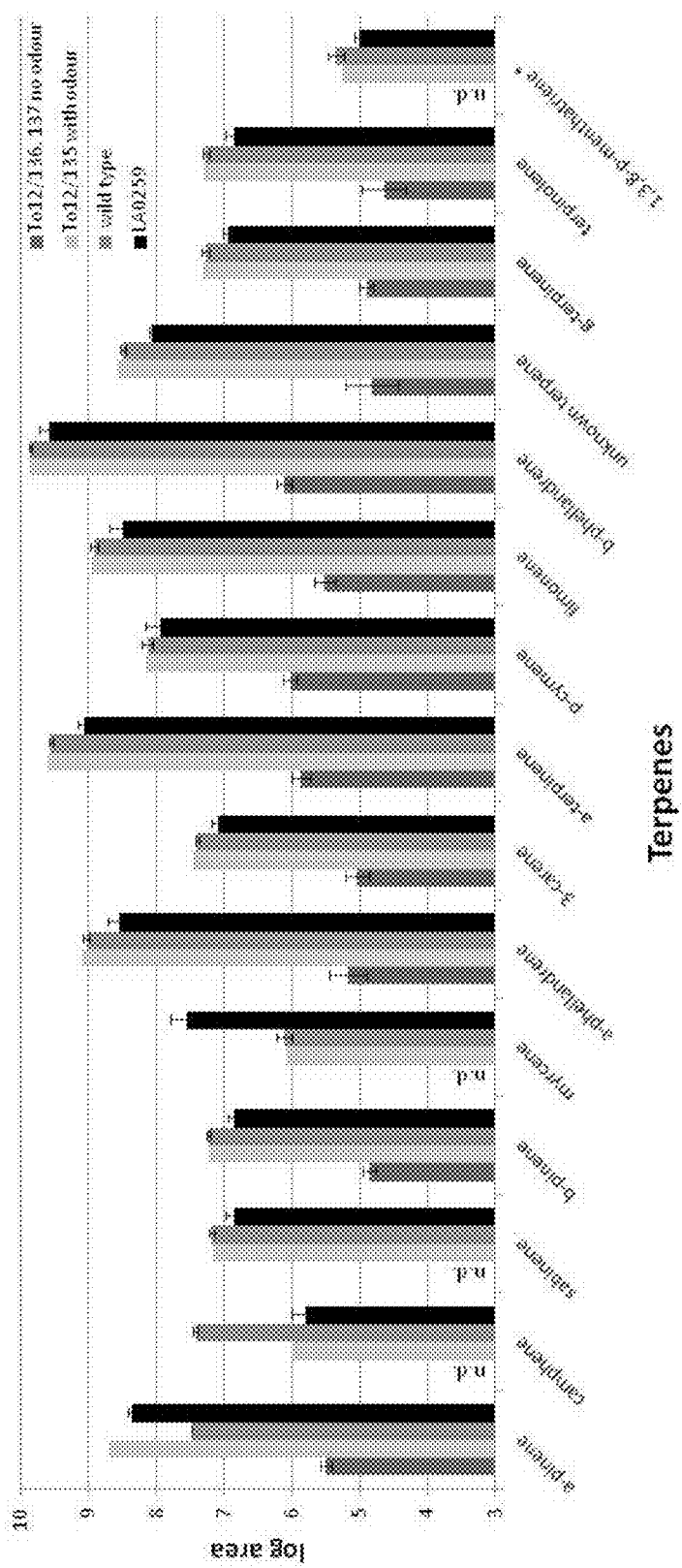
FIG. 8: Measurements in 2012 of various terpenes in plants of the invention (To12/136, 137) as compared to an isogenic plant (To12/135), normal wild-type tomato plants, and LA0259 (hl mutant); n.d.=not detected
Figure 9:
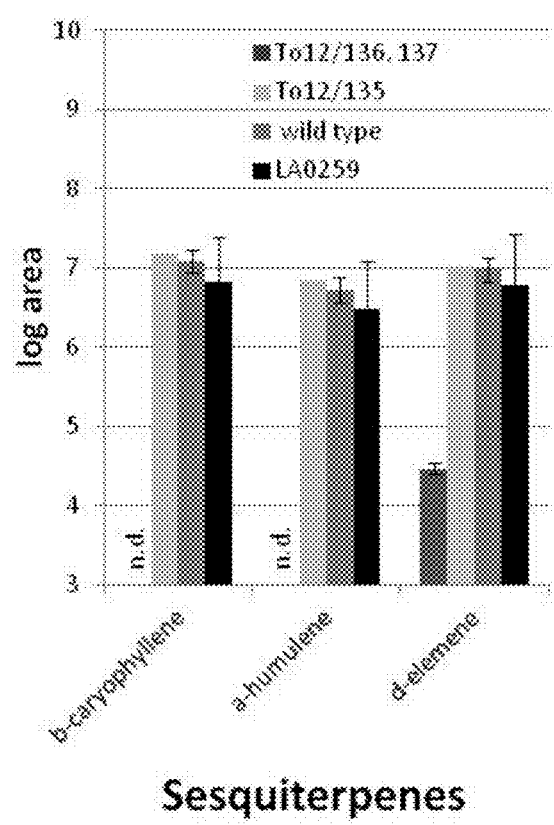
FIG. 9: Measurements in 2012 of various sesquiterpenes in plants of the invention (To12/136, 137) as compared to an isogenic plant (To12/135), normal wild-type tomato plants, and LA0259 (hl mutant); n.d.=not detected
Figure 10:
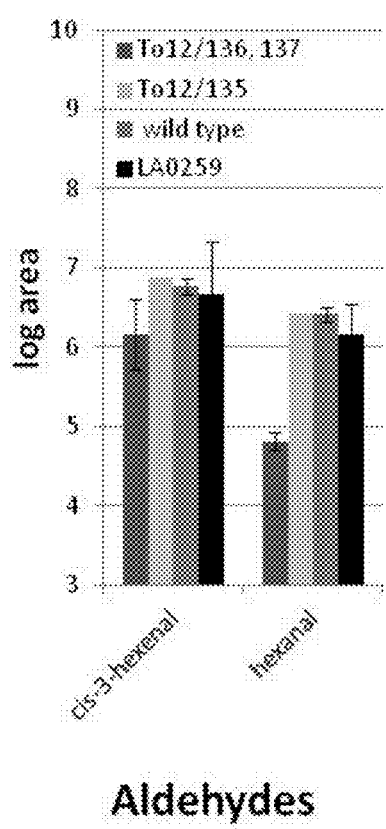
FIG. 10: Measurements in 2012 of various aldehydes in plants of the invention (To12/136, 137) as compared to an isogenic plant (To12/135), normal wild-type tomato plants, and LA0259 (hl mutant); n.d.=not detected
Figure 11:
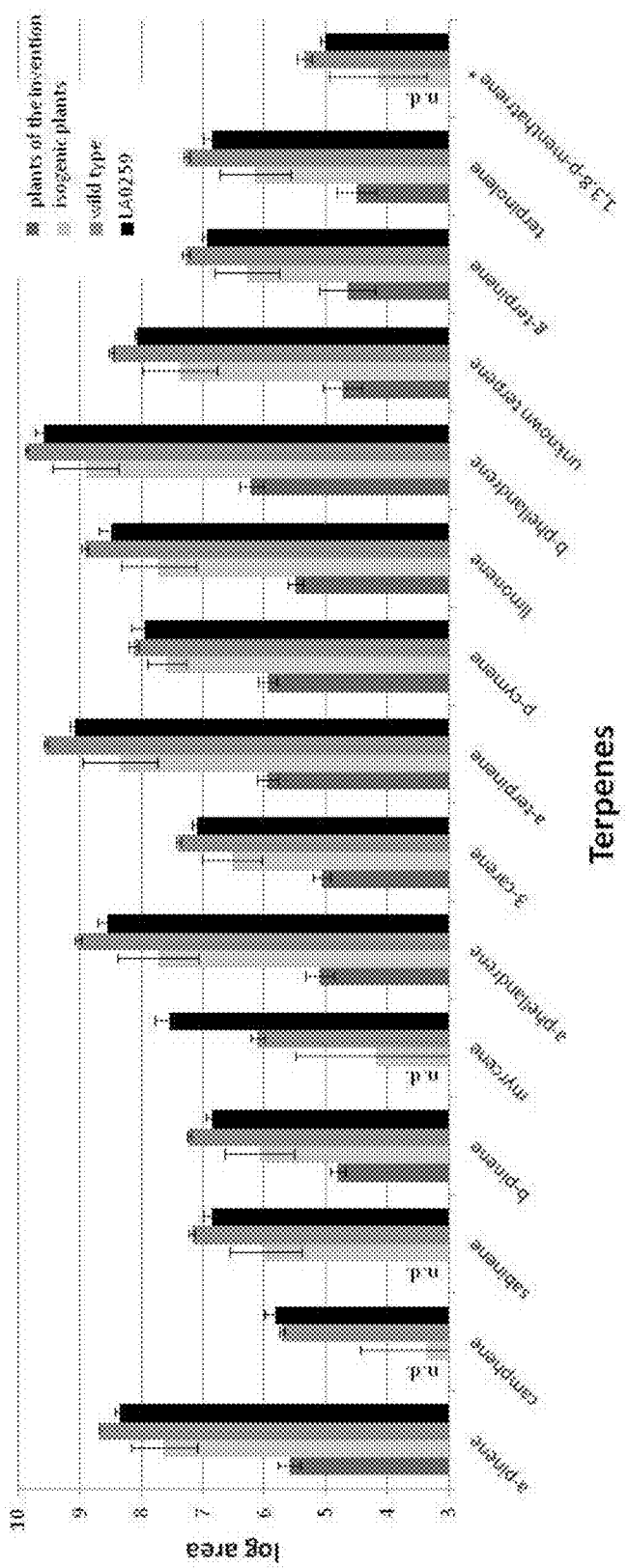
FIG. 11: Combined data of FIG. 3 and FIG. 8
FIG. 12: Combined data of FIG. 4 and FIG. 9
FIG. 13: Combined data of FIG. 5 and FIG. 10
FIG. 14: Unbalanced ANOVA of aldehyde measurement data.
Figure 12:
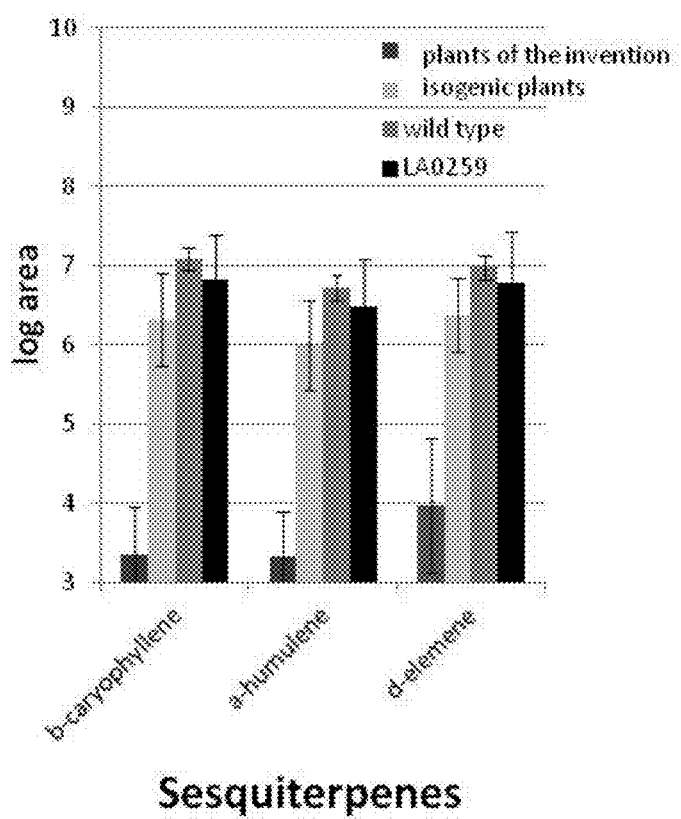
Figure 13:
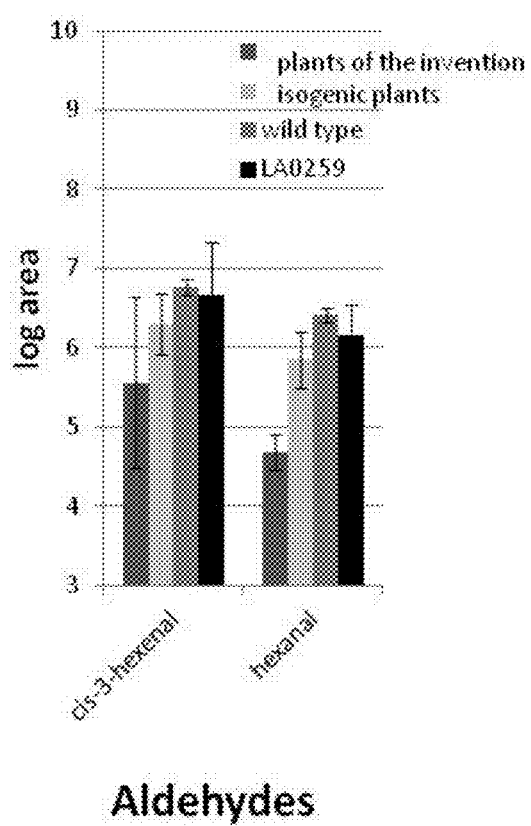

For all the terpenes that were measured, the areas were 100-10,000× reduced in plants of the invention as compared to other plants, including wild type and isogenic plants (FIGS. 3, 8, and 11). Also the sesquiterpenes showed a similar range of 100-10,000× area reduction in plants of the invention (FIGS. 4, 9, and 12).

As for the aldehydes, the compound cis-3-hexanal shows a significant 3-fold reduction for plants of the invention when the year is taken into account, which was calculated using an unbalanced ANOVA approach, and hexanal is about 40-fold reduced (FIGS. 5, 10, 13, and 14).

Plants belonging to the invention therefore showed a significant reduction in terpenes, sesquiterpenes and aldehydes, in addition to absence of type VI glands, absence of green staining, and absence or strong reduction of typical tomato smell.

Further experiments were done on the green staining that results from known tomato plants upon contact with the green vegetative parts. The staining of known tomato plants was analysed and compared with substances that are released upon contact with tomato plants of the invention. The absorbance of the staining particles was determined in ethanol extracts of the stem surface. As is well known by the person skilled in the art, green color in plants is characteristically determined by the presence of chlorophyll.

It was therefore highly surprising that analysis showed that none of the substances that were obtained from the tomato plants used in the experiment contained chlorophyll (EXAMPLE 6). Chlorophyll typically shows two absorbance peaks, one at around between 420 and 460 nm and one between around 620 and 700 nm, both of which were clearly absent in all extracts. Therefore it had to be concluded that the absence of green staining of tomato plants of the invention is not due to a change in chlorophyll content.

Also carotenoids, which account for or contribute to many coloured plant tissues, were not found among the substances that were analysed. Carotenoids have an absorbance peak between 400 and 500 nm, which is also clearly absent in all samples, as can be seen from FIG. 6. Both chlorophyll and carotenoids are water insoluble. So far, no differences were thus found in compounds that could potentially be responsible for the green staining.

Extracts from plants that do show green staining showed, however, a peak in the absorbance between around 355 and 370 nm, specifically at around 360 nm. This absorbance peak is known to relate to pigments belonging to the category of flavonoids.

Figures 6A, 6B:
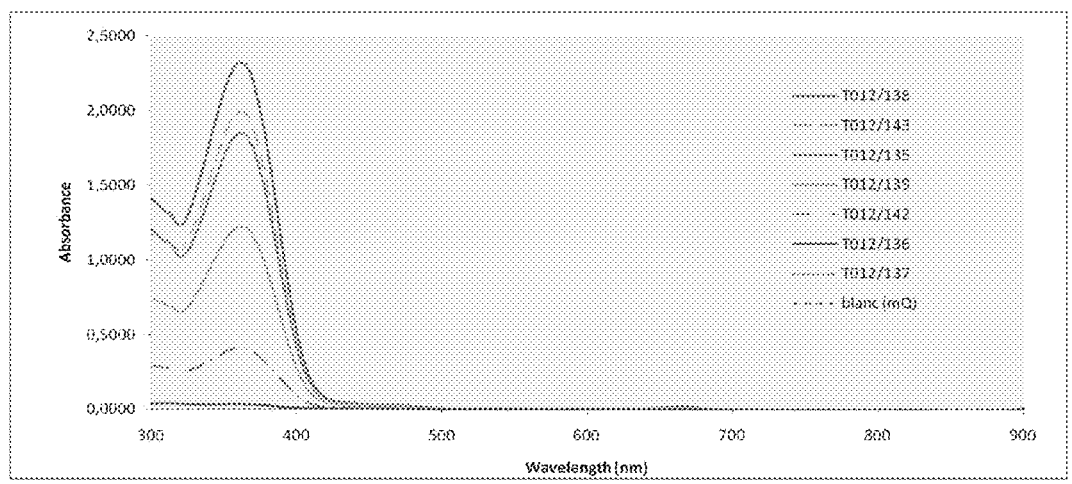
FIG. 6A-6B: Absorbance of tomato staining particles. The order of the accessions in the legenda is the order of the graph lines from top to bottom.

The absorbance of extracts from plants of the invention was below the detection threshold of 0.05. It was therefore established that tomato plants of the invention lack flavonoids, that are present in the staining obtained from the known tomato plants (FIG. 6, Table 1).

This additional research revealed that plants of the invention do not contain flavonoids that are present in the green vegetative parts of prior art tomato plants.

The invention thus provides a tomato plant that is characterized by the following features:
  the plant does not comprise or has at least a strongly reduced number of the glandular cells of type VI trichomes,
  the plant does not cause green staining upon contact,
    the plant has a strongly reduced level of volatiles, in particular terpenes, sesquiterpenes and aldehydes,
  the plant does not express or is at least strongly reduced in the typical tomato smell, and
  the plant does not comprise or has at least a strongly reduced level of flavonoids.

It was found according to the invention that these phenotypic parameters have a genetic basis in the form of a mutant allele.

Genetic mapping was carried out to determine the genetic location of the mutant allele and to confirm the number of genes involved (EXAMPLE 4). The mapping confirmed that the trait of the invention was the effect of a monogenic factor and one recessive mutant allele was involved. The mutant allele was named tghVI (tomato glandular hairless VI).

It was found according to the invention that the mutant tghVI allele leading to the phenotype of the invention is located on chromosome 9 of the tomato genome between the physical positions 1750800 bp and 4517648 bp, preferably between positions 1939546 bp and 2970346 bp, most preferably at about position 2454946 bp on the physical SL2.30 map of the *Solanum lycopersicum* genome.

The mutant tghVI allele may be identified by the presence of a molecular SNP marker that is linked to the tghVI allele. In deposit NCIMB 41845 a SNP marker linked to the tghVI allele is located at 1750800 bp on chromosome 9 of the physical *Solanum lycopersicum* map SL2.30 and is a nucleotide change from A to G.

The presence of the mutant tghVI allele in a plant of the invention is preferably also associated with a molecular SNP marker located on chromosome 9 at 1750800 bp on the public SL2.30 map of the *Solanum lycopersicum* genome, wherein the SNP is a nucleotide change from A to G. However, the absence of the SNP marker does not mean that the mutant allele is not present. A plant without the SNP marker but with the phenotype of the invention caused by the mutant allele may thus still be a plant of the invention.

The present invention thus provides a tomato plant (*Solanum lycopersicum*) which may comprise a mutant allele which allele is linked to the following phenotypic features:
  the plant does not comprise or has at least a strongly reduced number of the glandular cells of type VI trichomes,
  the plant does not cause green staining upon contact,
    the plant has a strongly reduced level of volatiles, in particular terpenes, sesquiterpenes and aldehydes,
  the plant does not express or is at least strongly reduced in the typical tomato smell, and
  the plant does not comprise or has at least a strongly reduced level of flavonoids.

Plants of the invention have modified type VI trichomes which modification leads to absent or non-functional type VI glandular cells or type VI glandular cells that do not function properly. The four glandular cells, i.e. the complete glandular head, are preferably completely absent. The trait of having modified type VI trichomes that lack all of the four glandular cells that make up the glandular head may for example be obtained from plants, representative seeds of which were deposited with the NCIMB under number NCIMB 41845, but the trait of lacking four glandular cells or having non-functional or mal-functioning glandular cells could also be obtained from other, yet unknown sources.

There had been no anticipation in the prior art that a single mutation would result in the absence of the glandular cells of type VI trichomes, and at the same time would generate a complete absence of staining and a strong reduction or lack of a typical tomato smell, and the invention is therefore highly surprising. The presence of various types of trichomes on tomato plants, and the perception that all glandular trichomes produce or store various substances that may be released, thereby potentially contributing to characteristics like aroma, color, exudate composition, and defense mechanisms, would not lead to the assumption that a single mutation could give such an enormous and varied effect.

The use of tomato plants of the invention leads to major advantages during tomato growing. The necessity to treat the skin with a substance in advance of handling tomato plants to prevent staining is removed. The use of protective clothing or gloves when working in a tomato crop is largely reduced. In addition, no rigorous methods to remove the staining after handling tomato plants are required anymore. The use of tomato plants of the invention will substantially facilitate tomato growing.

The absence of green staining and the reduction or absence of a typical tomato-plant aroma is the result of the modification in the composition of volatiles and flavonoids of a plant of the invention.

In one embodiment, the mutant tghVI allele is obtainable from a tomato plant which may comprise said mutant tghVI allele, representative seed of which was deposited with the NCIMB under deposit number NCIMB 41845.

In one embodiment, the tomato plant of the invention carrying the mutant tghVI allele is obtainable by crossing a first tomato plant with a second tomato plant, wherein one of the said plants is grown from seeds of which a representative sample was deposited with the NCIMB under deposit accession number NCIMB 41845, or a progeny plant thereof, and selecting, preferably in the F2 generation, for plants that show no green staining from the green vegetative parts of the plant upon contact, as compared to a plant not carrying the tghVI allele.

In one embodiment, one of the said plants used for crossing to obtain a tomato plant of the invention is carrying the tghVI allele.

Selection for plants which may comprise the tghVI allele may be done on phenotype, i.e. determining the presence of one or more of the phenotypic aspects of the trait, which are the absence of green staining, the absence or near absence of flavonoids, the reduction of volatiles, and the absence of a typical tomato smell. Furthermore selection may be done on the presence of modified type VI trichomes that lack glandular heads.

Selection may alternatively be done genetically on the presence of the relevant mutant tghVI allele, for example by using one or more molecular markers. The use of molecular markers results in a reliable outcome, and may be done in a very early plant stage.

The presence of the mutant tghVI allele also leads to the absence of the four glandular cells that form the glandular heads of type VI trichomes. The leaves of tomato plants of the invention are thus absent in fully developed type VI trichomes, and only possess type VI trichomes that lack glandular heads. Other glandular as well as non-glandular trichomes besides type VI may however be detected on a tomato plant of the invention.

The absence of glands of type VI trichomes is linked with the absence of green staining from the green vegetative parts of the plant upon contact. The green vegetative parts comprise the leaves and the stems of a plant. The presence of the tghVI allele preferably further leads to the absence of a typical tomato smell in a tomato plant of the invention. The absence of green staining and the absence of a typical tomato smell are the result of a modification in the composition of at least flavonoids and volatiles, due to the absence of glands of type VI trichomes.

In one embodiment, the mutant tghVI allele of the invention is present in homozygous form. The trait of the invention is monogenic, i.e. caused by a single gene, and is inherited in a recessive way. With respect to the trait of the invention, plants that carry the genetic trait, i.e. the mutant tghVI allele, may suitably be identified among descendants from a cross between a plant not carrying the trait, and a plant that does carry the said trait, by growing F2 plants from seeds that are the result of the initial cross and a selfing step, and selecting plants showing the desired trait. Selecting the plants may be done phenotypically by determining the absence of green staining, and/or the absence of a typical tomato smell, and/or the absence of flavonoids and/or the absence or reduction of volatiles and/or the absence of the glandular cells of type VI trichomes or may be done through identification of the mutant allele, for example by means of the marker defined herein.

Determining absence of green staining is done in comparison to a control. Suitably, the control to determine the absence of green staining is any existing tomato plant, or an isogenic tomato plant, i.e. a plant that is genetically identical to a plant of the invention, but does not carry the mutant tghVI allele that results in the trait of the invention.

In one embodiment selecting the plants in the F2 may be done phenotypically by determining the absence of the four glandular cells that form the glandular heads of type VI trichomes. The absence of glandular heads of type VI trichomes as mentioned throughout this application is determined on the green vegetative parts of the plant. The absence of glands of type VI trichomes should not be determined on the fruits.

The invention furthermore relates to a cell of a tomato plant as claimed. Such cell may be either in isolated form or may be part of the complete tomato plant or parts thereof and then still constitutes a cell of the invention because such a cell harbours in its genetic constitution the genetic information that leads to the characteristics that define the tomato plant of the invention. Each cell of tomato plants of the invention carries the genetic information that leads to phenotypic expression of said trait. Each cell thus carries the mutant tghVI allele in its genome.

The invention also relates to tissue of a plant as claimed. The tissue may be undifferentiated tissue or already differentiated tissue. Undifferentiated tissues are for example stem tips, anthers, petals, pollen and may be used in micropropagation to obtain new plantlets that are grown into new plants of the invention that have the above identified characteristics.

The invention according to a further aspect thereof relates to seeds of a plant as claimed. Although the seeds do not show the genetic trait of the tomato plant of the invention, they harbour the genetic information that when a plant is grown from the seeds makes this plant a plant of the invention that has the above identified characteristics.

The invention also relates to progeny of the plants, cells, tissues and seeds of the invention. Such progeny may in itself be plants, cells, tissues or seeds.

As used herein the word "progeny" is intended to mean the first and all further descendants from a cross with a plant of the invention that may comprise the mutant tghVI allele that leads to the absence of the glandular heads of type VI trichomes. Progeny of the invention are descendants of any cross with a plant of the invention that carries the trait that leads to the absence of the glandular heads of type VI trichomes or to the other characteristics identified above.

"Progeny" also encompasses plants that carry the trait of the invention and are obtained from other plants or progeny of plants of the invention by vegetative propagation or multiplication.

The invention thus further relates to seed of the claimed plant and to parts of the plant that are suitable for sexual reproduction. Such parts are for example selected from the group consisting of microspores, pollen, ovaries, ovules, embryo sacs and egg cells. In addition, the invention relates to parts of the plant that are suitable for vegetative reproduction, in particular cuttings, roots, stems, cells, and protoplasts.

According to a further aspect thereof the invention provides a tissue culture of the claimed plant. The tissue culture may comprise regenerable cells. Such tissue culture may be derived from leaves, pollen, embryos, cotyledons, hypocotyls, meristematic cells, roots, root tips, anthers, flowers, seeds and stems.

The invention furthermore relates to hybrid seed and to a method of producing hybrid seed which may comprise crossing a first parent plant with a second parent plant and harvesting the resultant hybrid seed, wherein said first parent plant and/or said second parent plant is the plant as claimed. Suitably in such hybrid seed the tghVI allele is present in homozygous form and the plant expresses the phenotype described above.

The invention also relates to inbreds and doubled haploids of tomato plants of the invention.

In one embodiment, the invention relates to tomato plants of the invention that carry the mutant tghVI allele, and having acquired said allele by introduction from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

The invention also relates to the germplasm of plants of the invention. The germplasm is constituted by all inherited characteristics of an organism and according to the invention encompasses at least the tghVI allele of the invention. The germplasm may be used in a breeding program for the development of tomato plants that are lacking in or have a reduction in green staining from the green vegetative parts of the plant upon contact, and/or are lacking a typical tomato plant aroma, and/or are absent in flavonoids from the green vegetative parts of the plant, and/or are reduced in volatile compounds, and/or are lacking glands of tomato type VI trichomes.

The invention also relates to a tomato fruit that is produced by a plant of the invention. The invention further relates to a food product, which may comprise the fruit of a tomato plant as claimed, or parts thereof. The invention also relates to a food product in processed form.

In one aspect the invention relates to a method for production of a tomato plant which may comprise the tghVI allele, which may comprise
a) crossing a plant which may comprise the mutant tghVI allele with another plant;
b) selfing the resulting F1 for obtaining F2 plants;
c) selecting plants which may comprise the tghVI allele in the F2;
d) optionally performing one or more additional rounds of selfing or crossing, and subsequently selecting for a plant which may comprise the tghVI allele.

It is clear that the parent that provides the trait of the invention is not necessarily a plant grown directly from the deposited seeds. The parent may also be a progeny plant from the seed or a progeny plant from seeds that are identified to have the trait of the invention by other means.

In one aspect, the invention relates to a method for production of a tomato plant which may comprise the tghVI allele, which may comprise
a) crossing a plant which may comprise the mutant tghVI allele that leads to the absence of the glandular heads of type VI trichomes with another plant;
b) optionally backcrossing the resulting F1 with the preferred parent;
c) selecting for plants which may comprise the tghVI allele which leads to the absence of glandular heads of type VI trichomes in the F2;
d) optionally performing one or more additional rounds of selfing or crossing, and subsequently selecting for a plant which may comprise the tghVI allele.

The invention additionally provides a method of introducing an additional desired trait into a tomato plant which may comprise the tghVI allele, which may comprise:
a) crossing a tomato plant which may comprise the tghVI allele, representative seed of which were deposited with the NCIMB under deposit number NCIMB 41845, with a second tomato plant that may comprise another desired trait to produce F1 progeny;
b) selecting an F1 progeny that may comprise the tghVI allele and the other desired trait;
c) crossing the selected F1 progeny with either parent, to produce backcross progeny;
d) selecting backcross progeny which may comprise the other desired trait and the tghVI allele; and
e) optionally repeating steps (c) and (d) one or more times in succession to produce selected fourth or higher backcross progeny that may comprise the other desired trait and the tghVI allele. The invention includes a tomato plant produced by this method.

In all these methods, the selection step is suitably done by means of marker analysis with the SNP marker described above. Alternatively, the selection may also or in addition be made on the basis of one or more of the phenotypic characteristics described above.

In one embodiment selection for plants which may comprise the tghVI allele is done in the F1. In another aspect selection for the trait of the invention is started in the F2 of a cross or alternatively of a backcross. Selection in the F1 is suitably done by means of the marker. Selection in the F2 may also be done on the basis of the phenotype.

In one embodiment selection for plants which may comprise the tghVI allele is started in the F3 or a later generation.

In one embodiment the plant which may comprise the mutant tghVI allele is a plant of an inbred line, a hybrid, a doubled haploid, or of a segregating population.

The invention further provides a method for the production of a tomato plant which may comprise the tghVI allele using a doubled haploid generation technique to generate a doubled haploid line which may comprise the said mutant tghVI allele that leads to the absence of the glandular heads of type VI trichomes, a modification in the composition of flavonoids and volatiles, absence of green staining, and/or absence of a typical tomato plant smell.

The invention furthermore relates to hybrid seed and to a method for producing hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid tomato plant which may comprise crossing a first parent tomato plant with a second parent tomato plant and harvesting the resultant hybrid tomato seed, in which the first parent tomato plant and/or the second parent tomato plant may comprise the mutant tghVI allele.

The invention also relates to a method for the production of a tomato plant which may comprise modification in the composition of flavonoids and volatiles, absence of the glandular heads of type VI trichomes, absence of green staining, and/or absence of a typical tomato plant smell, by using a seed that may comprise the mutant tghVI allele in its genome for growing the said tomato plant. The seeds are suitably seeds of which a representative sample was deposited with the NCIMB under deposit number NCIMB 41845.

The invention also relates to a method for seed production which may comprise growing tomato plants from seeds of which a representative sample was deposited with the NCIMB under deposit number NCIMB 41845, allowing the plants to produce seeds, and harvesting those seeds. Production of the seeds is suitably done by crossing or selfing.

In one embodiment, the invention relates to a method for the production of a tomato plant which may comprise the mutant tghVI allele by using tissue culture. The invention furthermore relates to a method for the production of a tomato plant which may comprise the mutant tghVI allele by using vegetative reproduction.

In one embodiment, the invention relates to a method for the production of a tomato plant which may comprise the mutant tghVI allele by using a method for genetic modification to introgress the mutant tghVI allele into the tomato plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of tomato plants that comprise modification in the composition of flavonoids and volatiles, absence of the glandular heads of type VI trichomes, absence of green staining, and/or absence or strong reduction of a typical tomato smell, wherein germplasm which may comprise the mutant tghVI allele is used. Representative seed of said plant which may comprise the mutant tghVI allele and being representative for the germplasm was deposited with the NCIMB under deposit number NCIMB 41845.

In a further embodiment the invention relates to a method for the production of a tomato plant which may comprise the mutant tghVI allele wherein progeny or propagation material of a plant which may comprise the mutant tghVI allele is used as a source to introgress the mutant tghVI allele into another tomato plant. Representative seed of said plant which may comprise the mutant tghVI allele was deposited with the NCIMB under deposit number NCIMB 41845.

The invention provides preferably a tomato plant showing modification in the composition of flavonoids and volatiles, absence of the glandular heads of type VI trichomes, absence of green staining, and/or absence or strong reduction of a typical tomato plant smell, which plant is obtainable by any of the methods herein described.

A mutant allele may be identified by the use of a molecular marker. A mutant allele may alternatively be identified by the position on a genetic map, or by indication of the location on a linkage group or chromosome. When a mutant allele is not linked to a specific molecular marker any longer, but its position on a chromosome as defined on a genetic map is unaltered, this mutant allele is still the same as when it was linked to the molecular marker. The genetic trait that it confers is therefore also still the same.

The 'genetic trait' is the trait or characteristic that is conferred by the mutant tghVI allele. The genetic trait may be identified phenotypically, for example by performing visual observations or biochemical analyses. However, also plant stages for which no phenotypic assay may be performed do carry the genetic information that leads to the genetic trait. 'Trait' or 'phenotypic trait' may be used instead of 'genetic trait'.

In the absence of molecular markers, equivalence to the mutant tghVI allele may be determined by an allelism test. To perform an allelism test, material that is homozygous for the tghVI allele is crossed with material that is homozygous for the mutant allele to be tested. When no segregation for the trait to be observed is present in the F2 of the cross, the unknown mutant allele has been proven to be the same as the tghVI allele.

Genetic maps may vary according to the method by which they are assembled. A person skilled in the art knows how to compare and combine genetic maps, whereby differences between genetic maps may be eliminated or minimized. Information from one genetic map may therefore be transferred or translated to another genetic map. The positions as used herein are physical positions based on the public physical map of the tomato genome SL2.30 (version of August 2010, http://solgenomics.net/organism/solanum_lycopersicum/genome).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Creation of Tomato Plants of the Invention

Seeds of two tomato breeding lines, TR306 and T029, were treated with ems (ethyl methane sulfonate) by submergence of approximately 10.000 seeds into an aerated solution of 0.5% (w/v) ems during 24 hours at room temperature.

The treated seeds were germinated and the resulting plants were grown in a greenhouse to produce M2 seeds.

After maturation, M2 seeds were harvested and bulked in one pool. The resulting pool of M2 seeds was used as starting material to identify individual M2 plants that were absent in green staining upon contact with the green vegetative plant parts.

The efficacy of the genetic modification procedure was assessed by determining the occurrence of bleached plants, which is indicative for chlorophyll loss due to modifications in genes directly or indirectly involved in the formation or accumulation of chlorophyll.

Example 2

Phenotypic Identification of a Plant of the Invention

M2 tomato seeds were germinated in soil and grown to small plantlets. Subsequently, approximately 7000 randomly chosen plants were transferred for a seedling screen.

Plants were touched to establish whether upon making contact the green vegetative parts would leave a yellowish or greenish substance on the skin. Three mutant plants were identified that, upon making contact, did not leave green staining. In addition, it was observed that the mutant plants did not give off the aroma that is typical for tomato plants. The mutant plants that were developed with this trait have the identification codes M2-2517, M2-4416, and M2-T029-mut. Seeds from M2-2517 were multiplied and resulted in population 11R-5000, which were deposited with the NCIMB under number NCIMB 41845.

The green plant parts of the mutant plants were visually observed by use of a binocular, and compared with normal wild type (WT) tomato plants. The microscopic observation showed that the glandular heads of type VI trichomes, which are made up of four glandular cells, were not present among the glands of the mutant tomato plants. It was therefore concluded that there was linkage between the absence of type VI glands and the absence of green staining Example 3

Transfer of the Trait of the Invention to Other Tomato Plants

Plants of the invention were crossed with wild type (WT) tomato plants, which do not carry the trait of the invention. The resulting F1 from this cross had the same phenotype as the WT plant, i.e. it did show green staining upon establishing contact. When the trichomes were observed, the F1 was found to have normal type VI trichomes, with the four glandular cells to form the glandular head.

The F2 segregated in a manner that corresponds with a monogenic recessive inheritance of the trait of the invention. Both the absence of green staining and the absence of four glandular cells of type VI trichomes segregated in the same way and both aspects were always observed together on the same plants, indicating there was co-segregation of the two aspects.

The trait of the invention could be brought into a wild type tomato plant by crossing the wild type plant with a plant of the invention and selecting for the desired phenotype in the F2 of that cross, either by selection on absence of green staining, or by selection on absence of four glandular cells of type VI trichomes.

Example 4

Genetic Mapping and Marker Development

A population of 90 F2 plants, as obtained from Example 3, were genotyped with 800 SNP markers. 329 of these SNP markers were reliably polymorphic and were used to do a QTL analysis for the absence of green staining. As expected for a monogenic trait, one mutant allele was located, positioned on chromosome 9. QTL mapping resulted in locating the mutant allele at around a physical position of 2454946 bp on the public SL2.30 map, with a LOD score of 41. For this position the mutant allele explained 88% of the variance of the trait, which confirms the monogenic nature.

The SNP marker that correlated most closely to the mutant allele is located on chromosome 9 at 1750800 bp on the public SL2.30 map of the *Solanum lycopersicum* genome, wherein the SNP is a nucleotide change from A to G. This molecular marker can be used to identify the presence of the mutant allele in plants grown from seeds as deposited under NCIMB number 41845.

The new mutant allele was provisionally named tghVI (tomato glandular hairless VI). Other plants that comprise the same mutant tghVI allele of the invention might also be linked to the A/G SNP on position 1750800 bp of the public SL2.30 map, but can optionally also be linked to another molecular SNP marker or any other molecular marker that is polymorphic in a certain population.

Example 5

Volatile Analysis of Plants of the Invention

Plants of the invention were analysed for a large number of volatiles, and compared with a tomato plant that did not contain the mutant tghVI allele of the invention. A tomato plant to be measured was placed in a plastic bag for 10 minutes. Next, the plants were touched to allow the release of the relevant compounds to be analysed. Subsequently Solid Phase Microextraction (SPME) was performed by introducing and exposing the fibre material to the gas inside the plastic bag for 15 minutes at room temperature.

After thermal desorption of the volatiles, three groups of compounds were analysed by using gas chromatography coupled to mass spectrometry (GC-MS): terpenes, sesquiterpenes, and aldehydes. Remarkably, for all the volatiles within these groups it was found that they were significantly reduced as compared to the wild type plant (FIG. 3-14). Some volatiles were even below detection level and therefore considered to be absent.

Example 6

Absorbance of Staining Particles

A number of tomato plants were analysed for the green staining. Included were plants of the invention, isogenic plants lacking the mutant allele of the invention, wild type (normal) tomato plants, and plants from the art that contain the hl (hairless) mutant allele (FIG. 6).

Plants were analysed at about 7-8 weeks after sowing. A metal spatula was used to wipe along the stem of each plant in the experiment, thus covering a surface area of approximately 75 cm$^2$. The resulting substance present on the spatula was dissolved in 1.0 ml ethanol. After drying the spatula, this procedure was repeated several times for each plant on different positions covering the whole stem surface.

The extracts from the individual plants were centrifuged for 5 minutes at 13000 rpm to remove debris, after which each extract was diluted with an equal volume of ethanol. A UV-VIS spectrophotometer was used to measure the absorbance of the solutions.

Although there were differences in the heights of the peaks of the plants that did not belong to the invention, all showed a maximum absorbance at the same wavelength of around 360 nm, indicating the same type of pigments. The absorbance at this wavelength indicates pigments belonging to the category of flavonoids.

There are various categories of flavonoids, which typically show a maximum absorbance at two different ranges of wavelengths, whereby the exact peak is depending on the number and type of the substituents that are bound to the basic flavonoid structure. The first absorbance peak is around between 210-290 nm, which is not in the visible part of the spectrum. The second absorbance peak can range between 300-400 nm or even up to 500 nm, which partly, from around 380 nm lies in the visible part of the spectrum. For plants of the invention, no absorbance at 360 nm was measured above the detection threshold of 0.05 (Table 1, FIG. 6).

TABLE 1

| | | | | Sample | | | | |
|---|---|---|---|---|---|---|---|---|
| | mq | To12/135 2* diluted | To12/136 2* diluted | To12/137 2* diluted | To12/138 2* diluted | To12/139 2* diluted | To12/142 2* diluted | To12/143 2* diluted |
| | | | | Cycle | | | | |
| | Cycle01 | Cycle01 | Cycle01 | Cycle01 | Cycle01 | Cycle01 | Cycle01 | Cycle01 |
| | | | | Entries | | | | |
| nm | Data Points blanc (mQ) | Data Points T012/135 | Data Points T012/136 | Data Points T012/137 | Data Points T012/138 | Data Points T012/139 | Data Points T012/142 | Data Points T012/143 |
| 300 | −0.0011 | 1.2034 | 0.0405 | 0.0328 | 1.4071 | 0.7397 | 0.2915 | 1.1767 |
| 301 | −0.0012 | 1.1995 | 0.0403 | 0.0323 | 1.4035 | 0.7383 | 0.2907 | 1.1735 |
| 302 | −0.0008 | 1.1955 | 0.0398 | 0.0319 | 1.3990 | 0.7362 | 0.2902 | 1.1696 |
| 303 | −0.0009 | 1.1890 | 0.0401 | 0.0329 | 1.3936 | 0.7334 | 0.2895 | 1.1646 |
| 304 | −0.0002 | 1.1829 | 0.0411 | 0.0327 | 1.3855 | 0.7304 | 0.2886 | 1.1589 |
| 305 | −0.0002 | 1.1740 | 0.0407 | 0.0332 | 1.3764 | 0.7257 | 0.2874 | 1.1521 |
| 306 | −0.0006 | 1.1635 | 0.0403 | 0.0327 | 1.3659 | 0.7197 | 0.2858 | 1.1439 |
| 307 | 0.0002 | 1.1534 | 0.0405 | 0.0335 | 1.3552 | 0.7143 | 0.2842 | 1.1370 |
| 308 | 0.0000 | 1.1438 | 0.0406 | 0.0333 | 1.3437 | 0.7085 | 0.2826 | 1.1296 |
| 309 | 0.0001 | 1.1363 | 0.0409 | 0.0338 | 1.3359 | 0.7045 | 0.2814 | 1.1243 |
| 310 | 0.0004 | 1.1299 | 0.0408 | 0.0339 | 1.3292 | 0.7009 | 0.2805 | 1.1205 |
| 311 | 0.0005 | 1.1245 | 0.0411 | 0.0340 | 1.3239 | 0.6985 | 0.2795 | 1.1177 |
| 312 | 0.0005 | 1.1185 | 0.0409 | 0.0337 | 1.3180 | 0.6954 | 0.2784 | 1.1137 |
| 313 | 0.0007 | 1.1093 | 0.0407 | 0.0337 | 1.3097 | 0.6912 | 0.2766 | 1.1089 |
| 314 | 0.0010 | 1.0971 | 0.0404 | 0.0336 | 1.2987 | 0.6852 | 0.2739 | 1.1016 |
| 315 | 0.0006 | 1.0850 | 0.0400 | 0.0335 | 1.2866 | 0.6787 | 0.2714 | 1.0941 |
| 316 | 0.0006 | 1.0713 | 0.0401 | 0.0335 | 1.2741 | 0.6725 | 0.2683 | 1.0867 |
| 317 | 0.0013 | 1.0555 | 0.0397 | 0.0334 | 1.2612 | 0.6651 | 0.2652 | 1.0777 |
| 318 | 0.0010 | 1.0401 | 0.0390 | 0.0325 | 1.2481 | 0.6582 | 0.2615 | 1.0709 |
| 319 | 0.0010 | 1.0290 | 0.0384 | 0.0322 | 1.2405 | 0.6529 | 0.2586 | 1.0663 |
| 320 | 0.0011 | 1.0225 | 0.0379 | 0.0318 | 1.2371 | 0.6513 | 0.2568 | 1.0664 |
| 321 | 0.0011 | 1.0203 | 0.0376 | 0.0314 | 1.2391 | 0.6515 | 0.2557 | 1.0696 |
| 322 | 0.0010 | 1.0233 | 0.0371 | 0.0309 | 1.2467 | 0.6558 | 0.2551 | 1.0780 |
| 323 | 0.0010 | 1.0306 | 0.0365 | 0.0306 | 1.2594 | 0.6623 | 0.2554 | 1.0897 |
| 324 | 0.0012 | 1.0399 | 0.0364 | 0.0300 | 1.2736 | 0.6697 | 0.2568 | 1.1026 |
| 325 | 0.0009 | 1.0532 | 0.0359 | 0.0299 | 1.2915 | 0.6789 | 0.2585 | 1.1178 |
| 326 | 0.0013 | 1.0699 | 0.0362 | 0.0299 | 1.3146 | 0.6913 | 0.2615 | 1.1375 |
| 327 | 0.0017 | 1.0880 | 0.0357 | 0.0300 | 1.3395 | 0.7045 | 0.2643 | 1.1594 |
| 328 | 0.0014 | 1.1083 | 0.0360 | 0.0296 | 1.3678 | 0.7192 | 0.2681 | 1.1824 |
| 329 | 0.0015 | 1.1315 | 0.0355 | 0.0294 | 1.3975 | 0.7352 | 0.2719 | 1.2090 |
| 330 | 0.0018 | 1.1541 | 0.0351 | 0.0290 | 1.4275 | 0.7511 | 0.2757 | 1.2344 |
| 331 | 0.0020 | 1.1794 | 0.0356 | 0.0292 | 1.4595 | 0.7683 | 0.2800 | 1.2621 |
| 332 | 0.0014 | 1.2037 | 0.0345 | 0.0283 | 1.4929 | 0.7853 | 0.2840 | 1.2896 |
| 333 | 0.0012 | 1.2286 | 0.0348 | 0.0282 | 1.5248 | 0.8023 | 0.2886 | 1.3171 |
| 334 | 0.0019 | 1.2530 | 0.0346 | 0.0280 | 1.5571 | 0.8197 | 0.2930 | 1.3441 |
| 335 | 0.0019 | 1.2798 | 0.0347 | 0.0284 | 1.5914 | 0.8378 | 0.2978 | 1.3739 |
| 336 | 0.0018 | 1.3070 | 0.0341 | 0.0278 | 1.6275 | 0.8565 | 0.3024 | 1.4036 |
| 337 | 0.0016 | 1.3353 | 0.0340 | 0.0277 | 1.6636 | 0.8761 | 0.3074 | 1.4346 |
| 338 | 0.0019 | 1.3636 | 0.0338 | 0.0275 | 1.7005 | 0.8947 | 0.3128 | 1.4654 |
| 339 | 0.0016 | 1.3914 | 0.0343 | 0.0274 | 1.7361 | 0.9135 | 0.3184 | 1.4958 |
| 340 | 0.0020 | 1.4208 | 0.0341 | 0.0278 | 1.7744 | 0.9329 | 0.3235 | 1.5261 |
| 341 | 0.0020 | 1.4503 | 0.0341 | 0.0279 | 1.8111 | 0.9531 | 0.3294 | 1.5590 |
| 342 | 0.0021 | 1.4801 | 0.0343 | 0.0276 | 1.8493 | 0.9727 | 0.3354 | 1.5907 |
| 343 | 0.0019 | 1.5069 | 0.0344 | 0.0279 | 1.8853 | 0.9910 | 0.3404 | 1.6209 |
| 344 | 0.0016 | 1.5347 | 0.0341 | 0.0277 | 1.9211 | 1.0102 | 0.3462 | 1.6523 |
| 345 | 0.0021 | 1.5615 | 0.0348 | 0.0284 | 1.9552 | 1.0280 | 0.3517 | 1.6811 |
| 346 | 0.0020 | 1.5862 | 0.0346 | 0.0282 | 1.9878 | 1.0449 | 0.3568 | 1.7072 |
| 347 | 0.0022 | 1.6138 | 0.0354 | 0.0286 | 2.0212 | 1.0628 | 0.3621 | 1.7362 |
| 348 | 0.0020 | 1.6404 | 0.0352 | 0.0285 | 2.0562 | 1.0807 | 0.3678 | 1.7657 |
| 349 | 0.0021 | 1.6670 | 0.0355 | 0.0288 | 2.0924 | 1.0990 | 0.3741 | 1.7944 |
| 350 | 0.0022 | 1.6921 | 0.0357 | 0.0288 | 2.1221 | 1.1157 | 0.3792 | 1.8216 |
| 351 | 0.0019 | 1.7138 | 0.0357 | 0.0284 | 2.1522 | 1.1298 | 0.3835 | 1.8444 |
| 352 | 0.0022 | 1.7368 | 0.0358 | 0.0293 | 2.1797 | 1.1453 | 0.3885 | 1.8682 |
| 353 | 0.0022 | 1.7583 | 0.0362 | 0.0291 | 2.2070 | 1.1594 | 0.3927 | 1.8913 |
| 354 | 0.0023 | 1.7763 | 0.0360 | 0.0297 | 2.2280 | 1.1714 | 0.3966 | 1.9118 |
| 355 | 0.0023 | 1.7928 | 0.0365 | 0.0297 | 2.2510 | 1.1829 | 0.4004 | 1.9292 |
| 356 | 0.0025 | 1.8087 | 0.0371 | 0.0295 | 2.2705 | 1.1934 | 0.4039 | 1.9462 |
| 357 | 0.0024 | 1.8213 | 0.0367 | 0.0298 | 2.2855 | 1.2018 | 0.4063 | 1.9604 |
| 358 | 0.0023 | 1.8313 | 0.0365 | 0.0293 | 2.2999 | 1.2084 | 0.4082 | 1.9700 |
| 359 | 0.0023 | 1.8392 | 0.0365 | 0.0296 | 2.3091 | 1.2134 | 0.4099 | 1.9784 |
| 360 | 0.0020 | 1.8459 | 0.0363 | 0.0293 | 2.3192 | 1.2176 | 0.4107 | 1.9855 |

TABLE 1-continued

| | | | | Sample | | | | |
|---|---|---|---|---|---|---|---|---|
| | mq | To12/135 2* diluted | To12/136 2* diluted | To12/137 2* diluted | To12/138 2* diluted | To12/139 2* diluted | To12/142 2* diluted | To12/143 2* diluted |
| | | | | | Cycle | | | |
| | Cycle01 | Cycle01 | Cycle01 | Cycle01 | Cycle01 | Cycle01 | Cycle01 | Cycle01 |
| | | | | | Entries | | | |
| nm | Data Points blanc (mQ) | Data Points T012/135 | Data Points T012/136 | Data Points T012/137 | Data Points T012/138 | Data Points T012/139 | Data Points T012/142 | Data Points T012/143 |
| 361 | 0.0023 | 1.8487 | 0.0365 | 0.0294 | 2.3225 | 1.2199 | 0.4113 | 1.9884 |
| 362 | 0.0019 | 1.8494 | 0.0362 | 0.0287 | 2.3239 | 1.2202 | 0.4104 | 1.9889 |
| 363 | 0.0025 | 1.8497 | 0.0361 | 0.0292 | 2.3228 | 1.2201 | 0.4105 | 1.9886 |
| 364 | 0.0024 | 1.8442 | 0.0352 | 0.0287 | 2.3174 | 1.2173 | 0.4094 | 1.9835 |
| 365 | 0.0023 | 1.8365 | 0.0346 | 0.0285 | 2.3092 | 1.2129 | 0.4073 | 1.9760 |
| 366 | 0.0024 | 1.8250 | 0.0349 | 0.0283 | 2.2941 | 1.2060 | 0.4048 | 1.9641 |
| 367 | 0.0022 | 1.8129 | 0.0345 | 0.0280 | 2.2790 | 1.1977 | 0.4018 | 1.9493 |
| 368 | 0.0024 | 1.7967 | 0.0342 | 0.0275 | 2.2604 | 1.1874 | 0.3981 | 1.9330 |
| 369 | 0.0025 | 1.7779 | 0.0338 | 0.0269 | 2.2374 | 1.1745 | 0.3935 | 1.9120 |
| 370 | 0.0021 | 1.7549 | 0.0329 | 0.0264 | 2.2057 | 1.1593 | 0.3879 | 1.8865 |
| 371 | 0.0021 | 1.7302 | 0.0323 | 0.0257 | 2.1763 | 1.1436 | 0.3820 | 1.8610 |
| 372 | 0.0025 | 1.6992 | 0.0327 | 0.0266 | 2.1291 | 1.1254 | 0.3769 | 1.8256 |
| 373 | 0.0025 | 1.6692 | 0.0320 | 0.0260 | 2.0916 | 1.1056 | 0.3704 | 1.7946 |
| 374 | 0.0027 | 1.6351 | 0.0319 | 0.0258 | 2.0516 | 1.0829 | 0.3631 | 1.7568 |
| 375 | 0.0024 | 1.5986 | 0.0307 | 0.0246 | 2.0057 | 1.0591 | 0.3545 | 1.7181 |
| 376 | 0.0025 | 1.5601 | 0.0297 | 0.0237 | 1.9574 | 1.0331 | 0.3457 | 1.6760 |
| 377 | 0.0022 | 1.5238 | 0.0292 | 0.0233 | 1.9130 | 1.0086 | 0.3369 | 1.6354 |
| 378 | 0.0022 | 1.4891 | 0.0287 | 0.0233 | 1.8678 | 0.9856 | 0.3295 | 1.5981 |
| 379 | 0.0025 | 1.4461 | 0.0276 | 0.0226 | 1.8139 | 0.9578 | 0.3202 | 1.5534 |
| 380 | 0.0026 | 1.3967 | 0.0269 | 0.0220 | 1.7517 | 0.9252 | 0.3090 | 1.4991 |
| 381 | 0.0027 | 1.3472 | 0.0258 | 0.0212 | 1.6918 | 0.8931 | 0.2981 | 1.4471 |
| 382 | 0.0027 | 1.2972 | 0.0248 | 0.0198 | 1.6293 | 0.8595 | 0.2864 | 1.3928 |
| 383 | 0.0019 | 1.2465 | 0.0235 | 0.0190 | 1.5665 | 0.8260 | 0.2741 | 1.3384 |
| 384 | 0.0027 | 1.1973 | 0.0226 | 0.0185 | 1.5053 | 0.7939 | 0.2635 | 1.2861 |
| 385 | 0.0023 | 1.1459 | 0.0214 | 0.0172 | 1.4405 | 0.7607 | 0.2520 | 1.2313 |
| 386 | 0.0022 | 1.0919 | 0.0203 | 0.0161 | 1.3708 | 0.7249 | 0.2395 | 1.1731 |
| 387 | 0.0027 | 1.0394 | 0.0194 | 0.0158 | 1.3063 | 0.6904 | 0.2278 | 1.1173 |
| 388 | 0.0022 | 0.9917 | 0.0178 | 0.0148 | 1.2455 | 0.6584 | 0.2166 | 1.0652 |
| 389 | 0.0025 | 0.9382 | 0.0171 | 0.0136 | 1.1790 | 0.6237 | 0.2050 | 1.0061 |
| 390 | 0.0021 | 0.8803 | 0.0163 | 0.0132 | 1.1060 | 0.5854 | 0.1919 | 0.9453 |
| 391 | 0.0025 | 0.8279 | 0.0154 | 0.0124 | 1.0402 | 0.5499 | 0.1802 | 0.8884 |
| 392 | 0.0022 | 0.7819 | 0.0145 | 0.0117 | 0.9826 | 0.5201 | 0.1701 | 0.8396 |
| 393 | 0.0024 | 0.7339 | 0.0140 | 0.0113 | 0.9218 | 0.4890 | 0.1599 | 0.7881 |
| 394 | 0.0026 | 0.6827 | 0.0129 | 0.0108 | 0.8573 | 0.4553 | 0.1487 | 0.7320 |
| 395 | 0.0024 | 0.6385 | 0.0127 | 0.0100 | 0.8018 | 0.4260 | 0.1392 | 0.6847 |
| 396 | 0.0025 | 0.5932 | 0.0119 | 0.0100 | 0.7446 | 0.3953 | 0.1292 | 0.6358 |
| 397 | 0.0021 | 0.5465 | 0.0113 | 0.0091 | 0.6832 | 0.3634 | 0.1186 | 0.5840 |
| 398 | 0.0021 | 0.5025 | 0.0103 | 0.0082 | 0.6284 | 0.3344 | 0.1090 | 0.5368 |
| 399 | 0.0024 | 0.4626 | 0.0101 | 0.0086 | 0.5779 | 0.3086 | 0.1006 | 0.4938 |
| 400 | 0.0021 | 0.4248 | 0.0096 | 0.0082 | 0.5299 | 0.2836 | 0.0925 | 0.4521 |

T012/135 isogenic plant
T012/136 plant of the invention
T012/137 plant of the invention
T012/138 wild type
T012/139 wild type
T012/142 LA0259 (hl)
T012/143 LA0259 (hl)

The staining of the tomato plants was also analysed for the presence of phenolic compounds. Flavonoids are a class of polyphenols, the presence of which can be determined by using Folin-Ciocalteu reagent.

The same diluted ethanol extract as was used for the absorbance measurements was used to measure the amount of phenolics. The phenolics are measured against a spectrophotometric standard, for which gallic acid was used. The measurement of phenolics was presented as gallic acid equivalents (GAE) in µg/g gallic acid (Table 2). From the table it can be derived that plants of the invention are significantly reduced in polyphenol content, which confirms the absence of flavonoids that was determined through the absorbance measurements.

TABLE 2

| accession | type | GAE |
|---|---|---|
| T012/135 | isogenic plant | 191 |
| T012/136 | plant of the invention | 29 |
| T012/137 | plant of the invention | 24 |
| T012/138 | wild type | 161 |
| T012/139 | wild type | 156 |
| T012/143 | LA0259 (hl) | 200 |

Phenolics are calculated as GAE in the extracts taken from the whole stem surface.

Example 7

Acyl Sugar Measurements

'Acyl sugars' or acylated sugars were thought to possibly contribute to the green staining from tomato plants, since they are known to be greasy or sticky compounds that do not dissolve in water. An experiment was set up to determine whether plants of the invention contained a reduction or absence of acyl sugars as compared to prior art tomato plants.

Acylated sugars are sugar compounds such as glucose or sucrose that are covalently bound to a fatty acid via an ester bond. To measure the acyl sugar contents in extracts taken from leaf discs, it was chosen to first detach the sugar and the fatty acid components. The bond between the components is broken by saponification, whereby hydrolysis of the ester bond takes place. After saponification the resulting sugar content can be measured.

The same accessions were used as in Example 6. Twelve leaf discs were taken with a cork borer of approximately 9.5 mm diameter. Discs were taken from the $2^{nd}$, $3^{rd}$ and $4^{th}$ leaf counted from the shoot apex of a plant, avoiding main veins, from plants of about 10-12 weeks old. Discs were placed in vials with 2 ml dichloromethane and rotated softly for 30 sec to dissolve surface compounds.

0.1 ml of leaf surface extract was evaporated under nitrogen gas and redissolved in 0.5 ml 0.1M NaOH solution in methanol. Samples were heated to 60° C. in a water bath for 15 min to allow saponification, i.e. breaking of the ester bond with NaOH and heat. Samples were then cooled and filtered.

No sugars could be detected in crude extracts before saponification, indicating that no sugars were dissolved from the leaf surface or leaking from wound surfaces. After saponification the sugar content was determined by Ion Exchange Chromatography on a Dionex HPLC. Concentration of sugars after saponification was then calculated to be equal to acylated sugars before saponification.

Figures 7A, 7B:
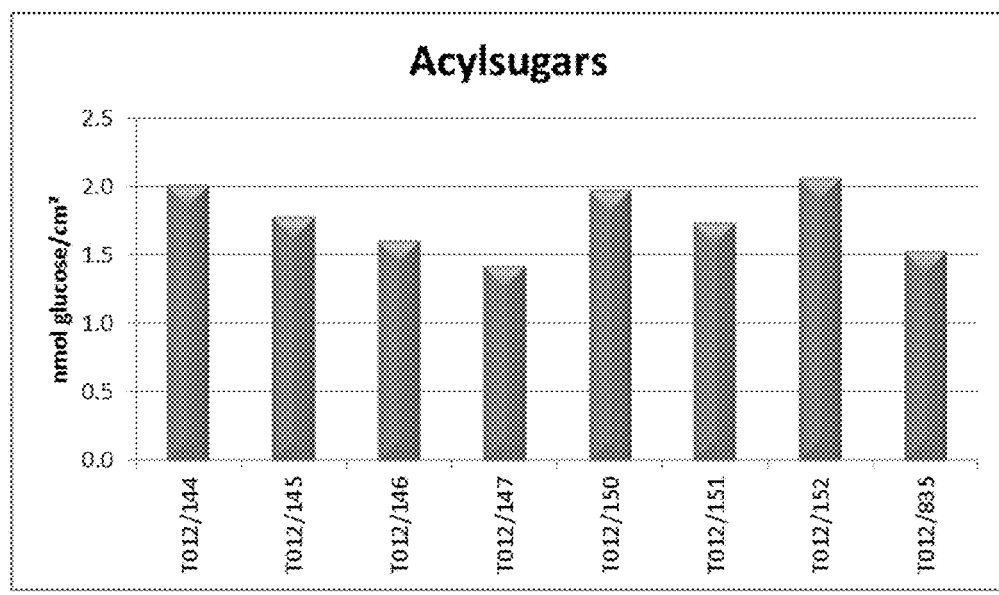
FIG. 7A-7B: Acyl sugar measurements. The results are given for glucose in nmol/cm$^2$ leaf disc.

No acylated sucrose could be identified in any of the samples. Acylated glucose was identified in all samples, and although there was variation, the differences were not significant (Students t-test P>0.1; FIG. 7). Plants of the invention ranked among the ones with the highest acylated glucose content, indicating that there was certainly no absence or strong reduction of acyl sugars involved in the trait of the invention.

The invention is defined in the claims that follow and is further described in the following numbered clauses:

1. Tomato plant (Solanum lycopersicum L.) comprising a mutant allele that leads to modification in the composition of flavonoids and volatiles as a result of the absence of the glandular heads of type VI trichomes, as compared to a plant not carrying the said genetic trait, which mutant allele is as comprised in a tomato plant representative seed of which was deposited with the NCIMB under deposit number NCIMB 41845.
2. Tomato plant as described in clause 1, wherein the said mutant allele is located on chromosome 9 between positions 1750800 bp and 4517648 bp, preferably between positions 1939546 bp and 2970346 bp, most preferably around position 2454946 bp on a physical map of the genome of Solanum lycopersicum.
3. Tomato plant as described in clause 1 or 2, obtainable by crossing a first tomato plant with a second tomato plant, wherein one of the said plants is grown from seeds as deposited with the NCIMB under deposit accession number NCIMB 41845, or a progeny plant thereof, and selecting, preferably in the F2 generation, for plants that are modified in the composition of flavonoids and volatiles as a result of the absence of the glandular heads of type VI trichomes, as compared to a plant not carrying the said genetic trait.
4. Tomato plant as described in clause 1 or 2, obtainable by crossing a first tomato plant with a second tomato plant, wherein one of the said plants is carrying the said genetic trait that results in modification in the composition of flavonoids and volatiles as a result of the absence of the glandular heads of type VI trichomes, and selecting, preferably in the F2 generation, for plants that are modified in the composition of flavonoids and volatiles as a result of the absence of the glandular heads of type VI trichomes, as compared to a plant not carrying the said genetic trait.
5. Tomato plant as described in any of the clauses 1 to 4, wherein the mutant allele leads to the absence of green staining from the green vegetative parts of the plant upon contact and/or the absence or reduction of a typical tomato aroma.
6. Seed of a tomato plant as described in any one of the clauses 1-5, wherein the plant that can be grown from the seed comprises the mutant allele as defined in clause 1 or 2.
7. Progeny of a tomato plant as described in any one of the clauses 1-5 or of tomato seed as described in clause 6, comprising the mutant allele as defined in clause 1 or 2.
8. Propagation material suitable for producing a plant as described in any one of the clauses 1-5 and 7 or seed as described in clause 6, wherein the propagation material is suitable for sexual reproduction, and is in particular selected from microspores, pollen, ovaries, ovules, embryo sacs and egg cells, or is suitable for vegetative reproduction, and is in particular selected from cuttings, roots, stems, cells, protoplasts, or is suitable for tissue cultures of regenerable cells, and is in particular selected from leaves, pollen, embryos, cotyledon, hypocotyls, meristematic cells, roots, root tips, anthers, flowers, seeds and stems, wherein a plant produced from the propagation material comprises the mutant allele as defined in clause 1 or 2.
9. Tomato plant as described in any of the clauses 1-5 and 7, seed as described in clause 6, or propagation material as described in clause 8, wherein the said mutant allele in the genome of seeds of which a representative sample was deposited as NCIMB 41845 is linked to a molecular SNP marker on position 1750800 of the public physical map SL2.30, wherein the SNP is a nucleotide change from A to G.
10. A tomato fruit of a plant as described in any one of the clauses 1-5 and 7.
11. Food product, comprising the tomato fruit as described in clause 10, or parts thereof, optionally in processed form.
12. Use of a plant as described in any one of the clauses 1-5, 7 and 9, or plants produced from the seed of clause 6, or from the propagation materials as described in clause 8 as germplasm in a breeding program for the development of tomato plants that are modified in the composition of flavonoids and volatiles as a result of the absence of the glandular heads of type VI trichomest, as compared to a plant not carrying the mutant allele of the invention.
13. Use of the mutant allele as defined in clause 1 or 2 for the development of tomato plants that are modified in the composition of flavonoids and volatiles as a result of the absence of the glandular heads of type VI trichomes.

14. Use of the molecular marker as defined in clause 9 for the development of tomato plants that are modified in the composition of flavonoids and volatiles as a result of the absence of the glandular heads of type VI trichomes.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A tomato plant that is characterized by the following features:
    as compared to a wild type or isogenic control plant, the plant does not comprise or has at least a reduced number of the glandular cells of type VI trichomes,
    as compared to a wild type or isogenic control plant, the plant has a reduced level of one or more terpenes, sesquiterpenes and/or aldehydes, and
    as compared to a wild type or isogenic control plant, the plant does not comprise or has at least a reduced level of flavonoids,
    wherein the plant carries a mutant tghVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G.

2. The tomato plant as claimed in claim 1, obtained by introgression of the mutant tghVI allele from a plant grown from seeds of which a representative sample was deposited under accession number NCIMB 41845 into a plant not carrying the allele.

3. A tomato seed that grows into the tomato plant as claimed in claim 1.

4. A seed of the tomato plant as claimed in claim 1, wherein the seed comprises at least one mutant tghVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G.

5. A progeny plant of the tomato plant as claimed in claim 1, wherein said progeny plant comprises at least one mutant tghVI allele.

6. A propagation material for producing the plant as claimed in claim 1 by sexual reproduction,
    wherein the propagation material comprises a microspore, pollen, ovary, ovule, embryo sac or egg cell,
    wherein the propagation material comprises at least one mutant tqhVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G, and
    wherein a plant produced from the propagation material comprises at least one mutant tghVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G.

7. A propagation material for producing the progeny plant as claimed in claim 5 by sexual reproduction,
    wherein the propagation material comprises a microspore, pollen, ovary, ovule, embryo sac or egg cell,
    wherein the propagation material comprises at least one mutant tghVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G, and
    wherein a progeny plant produced from the propagation material comprises at least one mutant tghVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G.

8. The progeny tomato plant as claimed in claim 5, characterized by the following features:
    as compared to a wild type or isogenic control plant, the plant does not comprise or has at least a reduced number of the glandular cells of type VI trichomes,
    as compared to a wild type or isogenic control plant, the plant has a reduced level of one or more terpenes, sesquiterpenes and/or aldehydes, and
    as compared to a wild type or isogenic control plant, the plant does not comprise or has at least a reduced level of flavonoids.

9. A tomato fruit of the plant as claimed in claim 1, wherein said fruit comprises at least one mutant tqhVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G.

10. A tomato fruit of the plant as claimed in claim 5, wherein said fruit comprises at least one mutant tqhVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G.

11. A food product comprising the tomato fruit as claimed in claim 9 or 10.

12. A breeding program method for developing tomato plants that comprise a mutant tghVI allele comprising the features defined in claim 1, comprising generating said tomato plants from germplasm from the tomato plant as claimed in claim 1.

13. A breeding program method for developing tomato plants that comprise a mutant tghVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G,
    wherein the tomato plants comprise the following features:
    as compared to a wild type or isogenic control plant, the plant does not comprise or has at least a reduced number of the glandular cells of type VI trichomes,
    as compared to a wild type or isogenic control plant, the plant has a reduced level of terpenes, sesquiterpenes and/or aldehydes, and as compared to a wild type or isogenic control plant, the plant does not comprise or has at least a reduced level of flavonoids, the method comprising generating said tomato plants from germplasm from the progeny tomato plant as claimed in claim 5.

14. A breeding program method for developing tomato plants that comprise a mutant tghVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G and comprising the features defined in claim 1, the method comprising generating said tomato plants from a germplasm with the mutant tghVI allele.

15. The breeding program method of claim 14, wherein said germplasm further comprises a molecular marker located at position 1750800 of the public physical map SL2.30, and wherein the marker is a SNP marker comprising a nucleotide change from A to G.

16. The tomato plant as claimed in claim 1, which is a *Solanum lycopersicum* L. plant.

17. A propagation material for producing the plant as claimed in claim 1 by vegetative reproduction, wherein the propagation material comprises a cutting, root, stem, cell or protoplast, and wherein a plant produced from the propagation material comprises at least one mutant tghVI allele on chromosome 9 which, in the genome of seeds of which a representative sample was deposited under accession number NCIMB 41845, is linked to a molecular SNP marker at position 1750800 of the public physical map SL2.30, wherein the SNP marker has a nucleotide change from A to G.

18. A propagation material for producing the plant as claimed in claim 1 by a tissue culture of regenerable cells, wherein the propagation material comprises a leaf, pollen, embryo, cotyledon, hypocotyl, meristematic cell, root, root tip, anther, flower, seed or stem, and wherein a plant produced from the propagation material comprises at least one mutant tghVI allele on chromosome 9 which, in the genome of seeds of which a representative sample was deposited under accession number NCIMB 41845, is linked to a molecular SNP marker at position 1750800 of the public physical map SL2.30, wherein the SNP marker has a nucleotide change from A to G.

19. A propagation material for producing the progeny plant as claimed in claim 5 by vegetative reproduction, wherein the propagation material comprises a cutting, root, stem, cell or protoplast, and wherein a progeny plant produced from the propagation material comprises at least one mutant tghVI allele on chromosome 9 which, in the genome of seeds of which a representative sample was deposited under accession number NCIMB 41845, is linked to a molecular SNP marker at position 1750800 of the public physical map SL2.30, wherein the SNP marker has a nucleotide change from A to G.

20. A propagation material for producing the progeny plant as claimed in claim 5 by a tissue culture of regenerable cells, wherein the propagation material comprises a leaf, pollen, embryo, cotyledon, hypocotyl, meristematic cell, root, root tip, anther, flower, seed or stem, and wherein a progeny plant produced from the propagation material comprises at least one mutant tghVI allele on chromosome 9 which, in the genome of seeds of which a representative sample was deposited under accession number NCIMB 41845, is linked to a molecular SNP marker at position 1750800 of the public physical map SL2.30, wherein the SNP marker has a nucleotide change from A to G.

21. A breeding program method for developing tomato plants that comprise a mutant tghVI allele on chromosome 9 which, in the genome of the seeds of which a representative sample was deposited under accession number NCIMB 41845, is linked to a molecular SNP marker at position 1750800 of the public physical map SL2.30, wherein the SNP marker has a nucleotide change from A to G and comprising the following features:

as compared to a wild type or isogenic control plant, the plant does not comprise or has at least a reduced number of the glandular cells of type VI trichomes, as compared to a wild type or isogenic control plant, the plant has a reduced level of one or more terpenes, sesquiterpenes and/or aldehydes, and as compared to a wild type or isogenic control plant, the plant does not comprise or has at least a reduced level of flavonoids, the method comprising generating said tomato plants from germplasm from the propagation materials as claimed in any one of claim 6, 7 or 17-20.

* * * * *